United States Patent [19]

Knowles et al.

[11] 4,220,590

[45] Sep. 2, 1980

[54] ASYMMETRIC CATALYSIS

[75] Inventors: William S. Knowles, St. Louis; Milton J. Sabacky, Ballwin; Billy D. Vineyard, St. Louis, all of Mo.

[73] Assignee: Monsanto Company, St. Louis, Mo.

[21] Appl. No.: 929,635

[22] Filed: Jul. 31, 1978

Related U.S. Application Data

[60] Division of Ser. No. 724,049, Sep. 16, 1976, Pat. No. 4,142,992, which is a division of Ser. No. 514,987, Oct. 15, 1974, Pat. No. 4,008,281, which is a continuation-in-part of Ser. No. 421,463, Dec. 3, 1973, abandoned.

[51] Int. Cl.² ............... C07C 101/02; C07C 103/50; C07D 209/20; C07D 233/64
[52] U.S. Cl. ............... 260/326.14 T; 562/444; 562/445; 260/347.4; 562/450; 562/561; 260/465 D; 562/562; 562/571; 260/558 A; 562/573; 562/575; 260/558 P; 260/558 R; 260/559 A; 260/559 R; 260/561 A; 260/561 K; 260/562 A; 260/562 K; 260/562 R; 548/344; 549/76; 549/77; 560/20; 560/21; 560/22; 560/23; 560/38; 560/39; 560/40; 560/41; 560/155; 560/171; 560/250; 560/251; 560/252; 562/434; 562/435; 562/437; 562/443

[58] Field of Search ............ 560/155, 40–41, 560/76, 171, 254, 20, 21, 22, 23, 38, 39, 250, 251, 252; 562/450, 445–446, 571, 575, 434, 435, 437, 443, 444, 561, 562, 573; 260/606.5 P, 429 R, 326.14 A, 326.14 T, 329 ME, 332.2 H, 340.5 R, 346.1 R, 465 D, 558 A, 558 P, 558 R, 561 A, 561 K, 501.11, 562 A, 562 K, 562 R, 347.4, 559 A, 559 R; 548/344; 549/76, 77

[56] References Cited

U.S. PATENT DOCUMENTS

| | | | |
|---|---|---|---|
| 3,798,241 | 3/1974 | Kagan et al. | 560/255 |
| 4,010,181 | 3/1977 | Aviron-Violet | 260/326.14 T |
| 4,124,533 | 11/1978 | Knowles et al. | 562/450 |

FOREIGN PATENT DOCUMENTS 937573 11/1973 Canada.

OTHER PUBLICATIONS

Emeleus, H. J. et al., "Advances in Inorganic Chemistry and Radio-chemistry," vol. 14 (1972) pp. 173, 174 & 241, Academic Press.

Maryanoff, Cynthia et al. "A One-Step Synthesis of Optically Pure 1,2-Ethano Bis Sulfoxides and Phosphine Oxides . . . . " J. Am. Chem. Soc. vol. 95 (Aug. 1973) 5839–5840.

*Primary Examiner*—Norman Morgenstern
*Assistant Examiner*—L. Hendriksen
*Attorney, Agent, or Firm*—Robert E. Wexler

[57] ABSTRACT

New optically active bis phosphine compounds which are usful in optically active catalysts. Such catalysts are particularly useful in catalytic asymmetric hydrogenation.

46 Claims, No Drawings

ASYMMETRIC CATALYSIS

This application is a division of Ser. No. 724,049, filed Sept. 16, 1976, now U.S. Pat. No. 4,142,992, which is a division of Ser. No. 514,987, filed Oct. 15, 1974, now U.S. Pat. No. 4,008,281 and which is a C-I-P of Ser. No. 421,463, filed Dec. 3, 1973, and now abandoned.

This invention relates to new optically active bis phosphine compounds which are useful in optically active catalysts which in turn are useful in catalytic asymmetric hydrogenation processes. More specifically, this invention is directed to new bis phosphine compounds and particularly 1,2-bis(o-anisylphenylphosphino)ethane, their precursor compounds, catalysts containing these new compounds and hydrogenation processes utilizing such catalysts.

Homogeneous catalysts, i.e. those catalysts that are soluble in the reaction mass, have been found to be particularly useful in processes wherein an asymmetric result is obtained. For instance, it has been found that when an olefin, which is capable of forming a racemic mixture is hydrogenated in the presence of an optically active homogeneous catalyst, one or the other of the possible desired optical enantiomorphs is obtained in a major amount with the other optical enantiomorph being obtained in minor amounts. Furthermore, it has been found that certain such olefinic substrates, for instance, precursors of α-amino acids, are particularly amenable to hydrogenation with homogeneous optically active catalysts. Such procedures are set forth more particularly in Canadian Pat. No. 937,573. Such catalytic asymmetric hydrogenation processes have resulted in the production of large amounts of the desired optical enantiomorph. Obviously any catalyst which produces such asymmetric hydrogenations would be useful.

It is an object of the present invention to provide such catalysts.

It is a further object to provide optically active phosphines which are useful in such catalysts. Still further, it is an object of this invention to provide catalytic asymmetric hydrogenation processes which are significantly superior in their ability to produce large amounts of the desired optical enantiomorph.

These and other objects, aspects and advantages of this invention will become apparent from a consideration of the accompanying specification and claims.

SUMMARY OF THE INVENTION

In accordance with the above objects, the present invention provides novel bis phosphine compounds, as hereinafter described, and their precursor dioxide compounds. These bis phosphine compounds, in optically active form, are useful in preparing coordination complex catalysts with metals selected from rhodium, iridium or ruthenium which, in turn, are useful in catalytic asymmetric hydrogenation processes of β-substituted-α-acylamido acrylic acids and/or their salts, esters or amides.

DESCRIPTION OF THE PREFERRED EMBODIMENTS

The present invention provides novel bis phosphine compounds which are characterized by the structural formula $$A-P(B)-CH_2CH_2-P(B)-A \qquad \text{I}$$

wherein A and B each independently represent substituted and unsubstituted alkyl of from 1 to 12 carbon atoms, substituted and unsubstituted cycloalkyl having from 4 to 7 carbon atoms, substituted and unsubstituted aryl; provided that such substituents provide no significant interference with the steric requirements around the phosphorus atom and A and B are different.

It has been found that these bis phosphine compounds, when used in a coordination complex catalyst in optically active form, possess the ability to produce catalytic asymmetric hydrogenation of a number of olefinic substrates which form an asymmetric carbon upon hydrogenation.

Among such bis phosphine compounds, those having two dissimilar aryl groups on each phosphorus atom are also preferred embodiments particularly those wherein one such aryl group has an alkoxy substituent at the ortho position.

Particularly preferred compounds of the present invention are characterized by the structural formula $$X-P(Y)-CH_2CH_2-P(Y)-X \qquad \text{II}$$

wherein
X represents substituted and unsubstituted phenyl,
Y represents substituted and unsubstituted 2-alkoxyphenyl wherein the alkoxy has from 1 to 6 carbon atoms; provided that such substituents provide no significant interference with the steric requirements around the phosphorus atom and X and Y are different.

Still more particularly preferred bis phosphine compounds of the present invention are characterized by the structural formula $$M-P(N)-CH_2CH_2-P(N)-M \qquad \text{III}$$

wherein M represents a phenyl ring with substituent $R_1$,

N represents a phenyl ring with substituents $R_3O$ and $R_2$, $R_1$ and $R_2$ each independently represent hydrogen, halogen, alkyl having from 1 to 6 carbon atoms and alkoxy having from 1 to 6 carbon atoms, and
$R_3$ represents normal alkyl having from 1 to 6 carbon atoms;
provided that M and N are different.

The novel precursor compounds characterized by the structural formula $$A-\overset{O}{\underset{B}{P}}-CH_2CH_2-\overset{O}{\underset{B}{P}}-A \qquad \text{IV}$$

wherein A and B have the same meaning as defined above, represent other embodiments of this invention. Likewise, such dioxide precursor compounds corresponding to the bis phosphine compounds of formulae II and III are preferred embodiments of this invention.

A particularly preferred novel compound provided by the present invention is 1,2-bis(o-anisylphenylphosphino)ethane which can readily be prepared from its precursor compound, 1,2-bis(o-anisylphenylphosphinyl)ethane.

Other exemplary bis phosphine compounds of this invention are:

1,2-bis(o-anisyl-4-methylphenylphosphino)ethane
1,2-bis(o-anisyl-4-chlorophenylphosphino)ethane
1,2-bis(o-anisyl-3-chlorophenylphosphino)ethane
1,2-bis(o-anisyl-4-bromophenylphosphino)ethane
1,2-bis[(2-methoxy-5-chlorophenyl)-phenylphosphino]ethane
1,2-bis[(2-methoxy-5-bromophenyl)-phenylphosphino]ethane
1,2-bis(2-ethoxyphenylphenylphosphino)ethane
1,2-bis[o-anisyl-(p-phenylphenyl)phosphino]ethane
1,2-bis[(2-methoxy-4-methylphenyl)-phenylphosphino]ethane
1,2-bis(2-ethoxyphenyl-4-chlorophenylphosphino)ethane
1,2-bis(o-anisyl-2-methylphenylphosphino)ethane
1,2-bis(o-anisyl-4-ethylphenylphosphino)ethane
1,2-bis(o-anisyl-3-ethylphenylphosphino)ethane
1,2-bis(o-anisyl-3-phenylphenylphosphino)ethane For these bis phosphine compounds to be useful in asymmetric hydrogenation reactions they must be utilized as the optically active enantiomorph and not in the meso form.

These novel optically active bis phosphine compounds can be prepared, for instance, by oxidative coupling of optically active phosphine oxide compounds prepared in a manner known to those skilled in the art and characterized by the structural formula

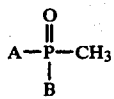

wherein A and B have the same meaning as defined above, in the presence of a suitable solvent, butyl lithium and a cupric salt.

Optically active catalysts prepared utilizing those novel optically active bis phosphine compounds of general formulae I and II provide useful catalytic asymmetric hydrogenation reactions giving the desired optical enantiomorph in major amounts.

Optically active catalysts prepared utilizing those novel optically active bis phosphine compounds of more specific formulae III provide particularly surprising and unexpected catalytic asymmetric hydrogenation reactions giving extremely large amounts of the desired optical enantiomorph.

Such optically active catalysts can be prepared by forming catalysts which contain a transition metal, such as rhodium, iridium and ruthenium, in combination with an optically active bis phosphine compound. The optically active catalysts of this invention are soluble coordination complexes comprising a metal selected from the group consisting of rhodium, iridium and ruthenium in combination with at least about 0.5 moles of an optically active bis phosphine ligand per mole of metal. Since these catalysts are soluble in the reaction mass they are referred to as "homogeneous" catalysts.

Optical activity of the coordinated complex catalysts, according to this invention, resides in the phosphine ligand. This optical activity results from having two different groups, in addition to the ethane bridge, on the phosphorus atom.

Illustrative coordination metal complexes can be represented by the formula MXL wherein M is a transition metal selected from the group consisting of rhodium, iridium and ruthenium; X is selected from the group consisting of hydrogen, fluorine, bromine, chlorine and iodine; L is the optically active bis phosphine ligand as previously defined.

It has been found that excellent yields of desired enantiomorphs can be achieved not only with the above described catalysts represented by the formula MXL, which are coordination complexes of a metal selected from the group consisting of rhodium, iridium and ruthenium, but can also be achieved when the hydogenation is carried out in the presence of a catalyst that comprises a solution of a transition metal selected from the group consisting of rhodium, iridium and ruthenium and at least about 0.5 moles of the optically active bis phosphine ligand per mole of metal. For instance, such catalysts can be prepared by dissolving a soluble metal compound in a suitable solvent together with a bis phosphine compound as the ligand wherein the ratio of ligand to metal is at least 0.5 moles of ligand per mole of metal, preferably one mole of ligand per mole of metal. Likewise, it has been found that the catalyst can be formed in situ by adding a soluble metal compound to the reaction mass together with the addition of the proper amount of the optically active ligand to the reaction mass either before or during hydrogenation.

The preferred metal to be utilized is rhodium. Soluble rhodium compounds that can be utilized include rhodium trichloride hydrate, rhodium tribromide hydrate, rhodium sulfate, organic rhodium complexes with ethylene, propylene, etc., and bis olefins such as 1,5-cyclooctadiene and 1,5-hexadiene, bicyclo-2.2.1-hepta-2,5-diene and other dienes which can form bidentate ligands, or an active form of metallic rhodium that is readily solubilized.

It has been found that the catalysts and processes of this invention are preferably those wherein the optically active bis phosphine ligand is present in a ratio of about 0.5 to about 2.0, preferably 1.0, moles of bis phosphine ligand per mole of metal. In practice, it is preferred to have the optically active catalyst in a solid form for purposes of handling and storage. It has been found that these results can be obtained with solid, cationic coordination metal complexes.

Cationic coordination metal complexes containing one mole of the optically active bis phosphine ligand per mole of metal and a chelating bis olefin represent preferred embodiments of the catalysts of the present invention. For instance, using organic rhodium complexes, as described above, one can prepare such cationic coordination rhodium complexes by slurrying the organic rhodium complex in an alcohol, such as ethanol, adding one mole per mole of rhodium of the optically active bis phosphine compound so that an ionic solution is formed, followed by the addition of a suitable anion, such as, for instance, tetrafluoroborate, tetraphenylborate or any other anion that will result in the precipitation or crystallization of a solid, cationic coordination metal complex either directly from the solvent or upon treatment in an appropriate solvent.

For instance, exemplary cationic coordination metal complexes are cyclooctadiene-1,5-[1,2-bis(o-anisylphenylphosphino)ethane]rhodium tetrafluoroborate, cyclooctadiene-1,5-[1,2-bis(o-anisylphenylphosphino)ethane]rhodium tetraphenylborate and bicyclo-2.2.1-hetpa-2,5-diene-[1,2-bis(o-anisylphenylphosphino)ethane]rhodium tetrafluoroborate.

Without prejudice to the present invention it is thought that the catalyst is present actually as a catalyst precursor and that upon contact with hydrogen the catalyst is converted to an active form. This conversion can, of course, be carried out during the actual hydrogenation or can be accomplished by subjecting the catalyst (or precursor) to hydrogen prior to addition to the reaction mass to be hydrogenated.

In general, such catalysts can be used to carry out catalytic asymmetric hydrogenation. It has also been found that certain olefins that result in unexpectedly high levels of the desired optical enantiomorph are the β-substituted- α-acylamidoacrylic acids and/or their salts, esters or amides. Such a reaction is illustrated by the following equation (wherein the β-substituent is phenyl):

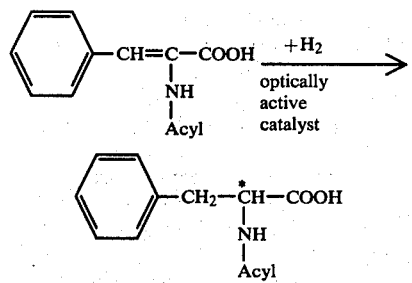

*shows the asymmetric carbon.

The β-substituent can be exemplified by such groups as hydrogen, alkyl, substituted alkyl, aryl, substituted aryl, aralkyl, amino, benzylamino, dibenzylamina, nitro, carboxyl and carboxylic ester, and the like. Those skilled in the art will recognize that the β-substituent can be selected from a large number of groups and that this is limited only by the α-amino acid that is the desired end-product.

Exemplary α-amino acids whose enantiomorphs can be expeditiously prepared in accordance with the process of this invention are alanine, p-chlorophenylalanine, tryptophan, phenylalanine, 3-(3,4-dihydroxyphenyl)-alanine, 5-hydroxytryptophan, halogenated tryptophans, lysine, histidine, tyrosine, leucine, glutamic acid and valine.

The acyl group can be substituted or unsubstituted acyl and can be exemplified by such groups as acetyl, benzoyl, formyl, propionyl, butyryl, toluyl, nitrobenzoyl, or other acyl variants commonly utilized as blocking groups in peptide synthesis, etc.

It is often preferred that such catalytic hydrogenation of the β-substituted-α-acylamido-acrylic acids be conducted in the presence of a base.

β-substituted- α-acylamido-acrylic acids and/or their salts, esters or amides are precursors of the substituted and unsubstituted alanines.

The compounds represented by the following structural formula provide excellent results with the process of this invention and therefore represent compounds particularly amenable to the present invention:

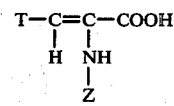

wherein, T is selected from the group consisting of hydrogen, carboxyl, unsubstituted and substituted alkyl, thienyl, β-indolyl, β-imidazolyl, furyl, piperonyl and

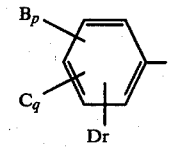

and B, C and D are independently selected from the group consisting of hydrogen, alkyl, carboxyl, hydroxyl (and their metal salts), alkoxy, halogen, acyloxy, aryloxy, aralkyloxy, amino alkyl amino, nitro, cyano, Z is selected from the group consisting of substituted or unsubstituted acyl, as described above, and p, q and r are integers of from 0 to 5 provided that the sum of p, q and r does not exceed 5.

A particularly preferred embodiment, which is also illustrative of the process of this invention, is the preparation of the substituted and unsubstituted phenylalanines by the catalytic asymmetric hydrogenation of the present invention. Unsaturated precursors of such α-amino acids can be prepared by the Erlenmeyer azlactone synthesis, wherein a substituted or unsubstituted benzaldehyde is reacted with an acylglycine, such as acetylglycine, and acetic anhydride to form the azlactone which is hydrolyzed to form the unsaturated precursor. Such a synthesis is illustrated by the following equations (utilizing benzaldehyde and acetylglycine as illustrative reactants):

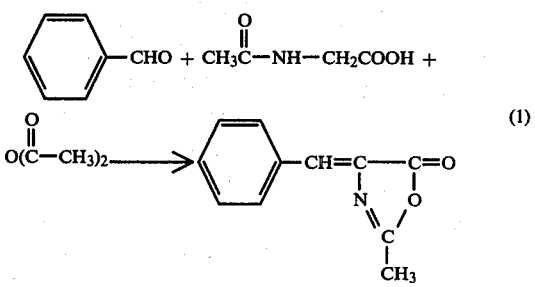

(1)

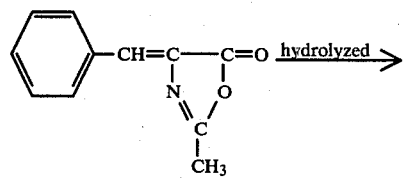

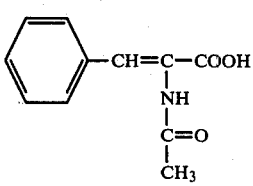

(2)

In such reactions the substituents on the phenyl group can be selected from a large number of groups and is limited only by the phenylalanine that is the desired end-product. Furthermore, it may occur that such substituent groups are themselves precursors or substituents that are desired in the end-product that can readily be converted to such desired substituents. For instance, if the substituted benzaldehyde is vanillin and one wishes to prepare one optical enantiomorph of 3-(3,4-dihydroxyphenyl)-alanine the unsaturated precursor might be α-acetamido-4-hydroxy-3-methoxy-cinnamic acid acetate which would provide the desired optical enantiomorph of N-acetyl-3-(4-hydroxy-3-methoxyphenyl)-alanine acetate upon hydrogenation which can then be converted to 3-(3,4-dihydroxyphenyl) alanine by simple hydrolysis.

The L enantiomorph of such phenylalanines are particularly desirable. For instance, 3-(3,4-dihydroxyphenyl)-L-alanine (L-DOPA) is well known for its usefulness in treating the symptoms of Parkinson's Disease. Likewise, L-phenylalanine has found use as an intermediate in the preparation of the alkyl esters of L-aspartyl-L-phenylalanine which have been recently recognized as excellent synthetic sweeteners.

Such hydrogenation reactions are usually conducted in a solvent, such as benzene, ethanol, 2-propanol, toluene, cyclohexane, and mixtures of these solvents. Almost any aromatic or saturated alkane or cycloalkane solvent, which is inactive to the hydrogenation conditions of this reaction, can be used. The preferred solvents are alcohols particularly aqueous methanol, ethanol and 2-propanol.

As previously noted, the catalyst is added to the solvent either as a compound per se or as its components which then form the catalyst in situ. When the catalyst is added as its components it may be added prior to or after the addition of the β-substituted- α-acylamido-acrylic acid. Components for the preparation of the catalyst in situ are the soluble metal compound and the optically active bis phosphine compound. The catalyst can be added in any effective catalytic amount and generally in the range of about 0.001% to about 5% by weight of contained metal based on the β-substituted-α-acylamidoacrylic acid (and/or their salts, esters or amides content).

Within the practical limits, means should be provided so as to avoid contacting the catalyst or reaction mass with oxidizing materials. In particular, care should be taken so as to avoid contact with oxygen. It is preferred to carry out the hydrogenation reaction preparation and actual reaction in gases (other than H₂) that are inert to both reactants and catalysts such as, for instance, nitrogen or argon.

As noted hereinbefore, it has been found that the asymmetric hydrogenation of acrylic acids is enhanced by the presence of a base in the reaction mass. Although the asymmetric hydrogenation can be carried out in a reaction mass that is free of base and even can be conducted under acidic conditions it is enhanced by the addition of a small amount, up to not more than one equivalent, of base material per mole of the acrylic acid.

Some bases that may be utilized are tertiary amines such as triethylamine, sodium hydroxide and generally any other basic material that will form a salt with carboxylic acid.

After addition of the reactants and catalyst to the solvent, hydrogen is added to the mixture until about 0.5 to about 5 times the mole quantity of the β-substituted-α-acylamido-acrylic acid present has been added. The pressure of the system will necessarily vary since it will be dependent upon the type of reactant, type of catalyst, size of hydrogenation apparatus, amount of reactants and catalyst and amount of solvent and/or base. Lower pressures, including atmospheric and subatmospheric pressure, can be used as well as higher pressures.

Reaction temperatures may be in the range of about $-20°$ C. to about $110°$ C. Higher temperatures may be used but are normally not required and may lead to an increase of side reactions.

Upon completion of the reaction which, is determined by conventional means, the product is recovered by conventional means.

Many naturally occurring products and medicaments exist in an optically active form. In these cases only the L or D form is usually effective. Synthetic preparation of these compounds in the past has required an additional step of separating the products into its enantiomorphs. This process is expensive and time consuming. The process of the present invention permits the direct formation of desired optical enantiomorphs in major amounts thus eliminating much of the time consuming and expensive separation of enantiomorphs. Furthermore, the process provides a higher yield of the desired optical enantiomorph while concurrently decreasing the yield of the unwanted enantiomorph.

Desired enantiomorphs of α-amino acids can be prepared by hydrogenating the proper β-substituted-α-acylamido-acrylic acid by the process of this invention followed by the removal of the acyl group on the α-amino and the other blocking groups by conventional means to yield the desired enantiomorph.

The bis phosphine compounds of this invention and the catalysts prepared therefrom are particularly desirable because of their ability to not only provide an unusually high optical purity of the desired optical enantiomorph but also because of their ability to afford a rapid rate of hydrogenation at low catalyst concentrations. Such catalysts exhibit excellent stability under higher hydrogen pressure allowing such rapid rates of hydrogenation.

The following examples will serve to illustrate certain specific embodiments within the scope of this invention and are not to be construed as limiting the scope thereof. In the examples, the percent optical purity is determined by the following equation (it being understood that the optical activity expressed as the specific rotations are measured in the same solvent):

% Optical purity = $\dfrac{\text{observed optical activity of the mixture} \times 100}{\text{optical activity of pure optical isomer}}$.

EXAMPLE 1

A solution of 34.0 g. ( 0.137 moles) of o-anisylmethylphenylphosphine oxide, $[\alpha]_D^{20}$ $+25.9°$ (C=1 in CH₃OH), in 500 ml. of tetrahydrofuran was cooled to $-60°$ C. At $-60°$ C. 68 ml. of butyl lithium in hexane (2.32 molar, 0.157 moles) was added and the mixture held at $-60°$ C. for 25 minutes. Then 22.3 g. (0.166 moles) of anhydrous CuCl₂ is added as a solid at $-50°$ to $-60°$ C. The mass is allowed to warm up to 20° C. over 1.5 hours and is finally held at 34° C. for 0.5 hour. At this point nmr indicates about 45% of unreacted o-anisylmethylphenylphosphine oxide is present. The reaction mass is treated by hydrolysis at 25°–30° C. with 100 ml. of 10% $H_2SO_4$. The copper salts were removed by adding 500 ml. of $CHCl_3$ and extracting with dilute aqueous ammonia. After drying the organic layer over $MgSO_4$ and evaporating the solvent 34 g. of an oil residue was obtained. Treatment with 50 ml. of acetone and 50 ml. of ether gave 9.0 g. of crystals. Recrystallization from the same solvent gave 7.0 g. of 1,2-bis(o-anisylphenylphosphinyl) ethane, m.p. 204°–5° C. $[\alpha]_D^{20}$ −44.2° (C=1 in $CH_3OH$). Mass spectra showed a parent peak at 490.

Reduction of 1,2-bis(o-anisylphenylphosphinyl) ethane was accomplished by refluxing 16.5 g. (0.12 mole) trichlorosilane and 12.2 g. (0.12 mole) triethylamine in 188 ml. of dry benzene for one hour. Then 3.0 g. (0.012 mole) of 1,2-bis(o-anisylphenylphosphinyl) ethane in 75 ml. of dry acetonitrile was added and the mixture refluxed 1.5 hours. Quenching in 30% sodium hydroxide solution followed by separating and evaporating the organic layer gave 1.4 g. of crude crystals which were insoluble in cold methanol. Further crystallization from hot methanol gave 1,2-bis(o-anisylphenylphosphino) ethane, m.p. 102°–104° C., $[\alpha]_D^{20}$ −83.4° (C=0.5 in $CHCl_3$). The mass spectra gave a very strong parent peak at 458 and the nmr confirmed the structure.

EXAMPLE 2

To a slurry of 4.43 g. (18 meq.) bis(cyclooctadiene-1,5)-dichlorodirhodium ([Rh(COD)Cl]₂) in 50 ml. of ethere was added 1.80 g. (18 m moles) acetylacetone in 25 ml. ether at 25° C. The mixture was cooled to −75° C. and 11 ml. of 25% potassium hydroxide solution was added. The batch was warmed to 0° C. and 75 ml. more ether added and stirred 0.5 hours.

The resulting mixture was filtered and the filtrate was treated with $MgSO_4$ to remove water anc concentrated to 125 ml. It was then chilled to −75° C. and the resulting crystals filtered to give 4.34 g. of rhodium (cyclooctadiene-1,5) acetylacetonate.

Then 125 mg. (0.4 m moles) of rhodium (cyclooctadiene-1,5) acetylacetonate and 184 mg. of the 1,2-bis(o-anisylphenylphosphino) ethane prepared in Example 1 (0.4 m moles) was stirred in 2.5 ml. methanol. After stirring for 45 minutes a red-orange solution was formed. To this solution was added dropwise 88 mg. (0.8 m moles) of sodium tetrafluoroborate in 1.25 ml. $H_2O$. The precipitate formed was filtered and washed with water and ether giving 202 mg. of cyclooctadiene-1,5-[1,2-bis(o-anisylphenylphosphino) ethane]rhodium tetrafluoroborate.

EXAMPLE 3

A solution of 0.013 g. of [Rh(COD)Cl]₂ (0.026 m moles) and 0.024 g. 1,2-bis(o-anisylphenylphosphino) ethane prepared in Example 1 (0.051 m moles) in 5 ml. of methanol was made with stirring for 15 minutes at 25° C. With careful exclusion of air, 0.5 ml. of this solution was added to a slurry of 1.00 g. of α-acetamidocinnamic acid in 25 ml. of 88% i-propanol at 50° C. and the resulting mass was subjected to 3.5 atm. (abs. pressure) of hydrogen. The hydrogenation reaction was completed in 0.7 hours. N-acetyl-L-phenylalanine can be isolated from the reaction mass by crystallization. Analysis of the reaction mixture showed that an optical purity of 92.8% of the L isomer was obtained.

EXAMPLE 4

A solution of 100.0 g. (0.487 moles) of α-acetamidocinnamic acid in 100 ml. of methanol, 81.5 ml. of water and 37.0 g. of 50% sodium hydroxide (0.463 moles) was thoroughly purged to remove oxygen. Then at 50° C. and under 40 psig. of hydrogen the catalyst solution which consisted of 0.0368 g. of the cyclooctadiene-1,5-[1,2-bis(o-anisylphenylphosphino) ethane]rhodium tetrafluoroborate prepared as in Example 2 in 2 ml. of methanol was injected through a septum. Hydrogenation was complete in 9 hours giving an optical purity of 95–96%. The product was isolated from its sodium salt by addition of 45.7 g. (0.463 moles) of 37% HCl. There was obtained 94.0 g. of N-acetyl-L-phenylalanine, $[\alpha]_D^{20}$ +47.1° (C=1 in 95% ethanol).

EXAMPLE 5

Other hydrogenation reactions were carried out using procedures similar to those used in Examples 3 and 4 as shown in Table I below. All hydrogenations were run with 0.05% rhodium concentrations based on the weight of the olefin being hydrogenated.

TABLE I

| Olefin | Solvent | Temperature (°C.) | Abs. Press. (atm.) | Reaction Time (hrs.) | % Optical Purity |
|---|---|---|---|---|---|
| 3-methoxy-4-hydroxy-α-[a] acetamido cinnamic acid acetate | Methanol | 50 | 3.5 | 1.0 | 89.4 |
| 3-methoxy-4-hydroxy-α-[b] acetamido cinnamic acid acetate | Methanol | 50 | 3.5 | 1.5 | 89.5 |
| 3-methoxy-4-hydroxy-α-[b] acetamido cinnamic acid acetate | Methanol | 25 | 3.5 | 4.0 | 90.9 |
| 3-methoxy-4-hydroxy-α-[b] acetamido cinnamic acid acetate | 88% 2-propanol | 50 | 3.5 | 0.7 | 92.8 |
| α-acetamidocinnamic acid[b] | 88% 2-propanol | 25 | 3.5 | 3.0 | 92.8 |
| α-acetamidocinnamic acid[b] | 88% 2-propanol | 50 | 3.5 | 0.8 | 93.8 |
| α-acetamidocinnamic acid[b] | 88% 2-propanol | 25 | 27.0 | 0.8 | 91.8 |
| α-acetamidocinnamic acid[b] | 50% methanol[c] | 25 | 4.0 | 4.0 | 95.7 |
| α-acetamidocinnamic acid[b] | 50% methanol[c] | 50 | 4.0 | 1.3 | 96.2 |
| α-acetamidocinnamic acid[b] | 50% methanol[c] | 50 | 4.0 | 1.3 | 95.1 |
| α-acetamidocinnamic acid[b] | 50% methanol[c] | 25 | 27.0 | 1.0 | 95.5 |
| N-acetyl-indolyl-α-[b] | | | | | |

TABLE I-continued

| Olefin | Solvent | Temperature (°C.) | Abs. Press. (atm.) | Reaction Time (hrs.) | % Optical Purity |
|---|---|---|---|---|---|
| acetamidoacrylic acid | Methanol | 50 | 4.0 | 0.75 | 93.5 |

Footnotes for Table I:
[a]Catalyst generated in situ (similar to Example 3)
[b]Catalyst prepared as a complex (similar to Example 4)
[c]Carried out in the presence of 0.95 equivalents of sodium hydroxide based on the acrylic acid present
[d]All optical activities were measured without isolation by diluting to volume and comparing with a blank, taking for pure N-acetyl-L-phenylalanine $[\alpha]_D^{20} + 47.5°$ (C = 1 in 95% ethanol), N-acetyl-3-(4-hydroxy-3-methoxyphenyl)-L-alanine acetate $[\alpha]_D^{20} + 40.8°$ (C = 1 in CH$_3$OH) and 3-(N-acetylindolyl)-N-acetyl-L-alanine $[\alpha]_D^{20} + 35.1°$ (C = 0.5 in CH$_3$OH). In no case was the catalyst contribution more than 2%.

EXAMPLE 6

To a solution of 49.2 g. (0.20 mole) of o-anisylmethylphenyl phosphine oxide $[\alpha]_D^{20} + 25.9°$ (C=1 in CH$_3$OH) in 100 ml. of tetrahydrofuran at 5° C. is added a solution of lithium diisopropylamide, prepared by adding 91.6 ml. of 2.4 N butyllithium in hexane to 24.5 g. (0.24 mole) di-isopropylamine in 100 ml. tetrahydrofuran. After a 0.5 hour addition period the batch is stirred 0.5 hour at 0°–5° C. 20.0 g. (0.20 equiv.) of Cu$_2$Cl$_2$ is then added at 0°–5° C. After a 0.5 hour period of stirring, 26.9 g. (0.2 mole) of CuCl$_2$ is added while maintaining the temperature at 0°–5° C. The reaction mass is then warmed over one hour to 20°–25° C. and held at that temperature for 0.5 hour. It is subsequently quenched with 100 ml. of concentrated HCl at 15°–20° C. After settling, the upper hexane layer is discarded. The organics are extracted with chloroform, the chloroform layer washed free of copper salts with 10% HCl and finally with water. The organic layer is stripped of chloroform up to a temperature of 95° C. and 200 ml. of n-butyl acetate is added. The resulting mass, which is now a slurry of crystals, is heated to 116° C. to remove the remaining traces of chloroform and slowly cooled to 0°–5° C. The product is filtered and washed with 50 ml. of cold butyl acetate and dried at 100° C. and 200 mm. Hg.

The yield is 33.5 g. of 1,2-bis(o-anisylphenylphosphinyl) ethane, m.p. 203°–5° C. $[\alpha]_D^{20} - 44.9°$ (C=1 in CH$_3$OH) Pure 1,2-bis(o-anisylphenylphosphinyl) ethane melts at 205°–7° C., $[\alpha]_D^{20} - 46.0°$.

Reduction of 1,2-bis(o-anisylphenylphosphinyl) ethane is accomplished by dissolving, under N$_2$,60.0 g. (0.122 mole) of 1,2-bis(o-anisylphenylphosphinyl) ethane in 450 ml. of dry acetonitrile. 150 g. of dry tributylamine is subsequently added and the resulting slurry is heated to 65°–70° C. until a solution is formed. 97. g. of trichlorosilane is added to the resulting solution over a one hour period, keeping the temperature at 70°–72° C. At the completion of the ensuing reaction there is essentially one liquid phase which is held at 70° C. for 2 hours and then cooled to 30°–40° C. quenched by adding, at 25°–30° C., to 360 ml. of 25% aqueous sodium hydroxide. At the end of the quench the temperature is raised to 45°–50° C. to facilitate layer separation.

The organic phase is separated and washed under N$_2$ with an additional 150 ml. of 25% aqueous sodium hydroxide. The organic phase, which consists of two layers is concentrated at 45°–55° C. until only the high boiling tributylamine remains. At this point a small amount (50 ml.) of benzene was added and the temperature raised to 75° C. at 40 mm. Hg. pressure. 50 ml. of methanol is added to aid crystallization and the batch is cooled to 0°–5° C. and filtered. The cake is washed with two 40 ml. portions of cold methanol and dried at 60° C. and 1 mm. Hg. giving 50.8 g. of 1,2-bis(o-anisylphenylphosphino) ethane, m.p. 96°–101° C., $[\alpha]_D^{20} - 79.7°$. Recrystallization from hot methanol gives a pure product melting at 102°–4° C., $[\alpha]_D^{20} - 85.0°$. This material can be used directly for an in situ catalyst preparation but is more conveniently converted to a rhodium complex as follows.

A slurry of 1.83 g. (4.0 m moles) of 1,2-bis(o-anisylphenylphosphino) ethane was added to 12 ml. of 90% methanol. Under nitrogen at 25°–30° C., 0.99 g. (2.0 m moles) of bis(cyclooctadiene-1,5)-dichlorodirhodium ([Rh(COD)Cl]$_2$) was added. The resulting slurry becomes orange and, after stirring for one hour, gives a red-orange solution. The desired complex is precipitated by adding slowly a solution 0.66 g. (6.0 m moles) of sodium tetrafluoroborate in 5 ml. of H$_2$O over two hours. After one hour stirring at 25° C. the fine crystals are filtered and washed twice with 3 ml. portions of water, and dried at 5 mm. Hg. and 25° C. There was obtained 2.8 g. of cyclooctadiene-1,5-[1,2-bis(o-anisylphenylphosphino) ethane]rhodium tetrafluoroborate which is a 90% yield.

EXAMPLE 7

Following a procedure similar to that of Example 6, the compounds 1,2-bis(o-anisylethylphosphinyl) ethane, m.p. 188°–9° C. $[\alpha]_D^{20} - 76.1°$ (C=1 in CH$_3$OH) and 1,2-bis(o-anisylethylphosphino) ethane, an oily material were prepared.

EXAMPLE 8

Following a procedure similar to that of Example 6, the compounds 1,2-bis(o-anisylcyclohexylphosphinyl) ethane, m.p. 221°–6° C. $[\alpha]_D^{20} - 50.8°$ (C=1 in CH$_3$OH) and 1,2-bis(o-anisyl cyclohexylphsophino) ethane, m.p. 69°–74° C. were prepared.

EXAMPLE 9

Using an in situ catalyst preparation with rhodium and the bis phosphine compounds of Examples 7 and 8 and hydrogenating α-acetamido-cinnamic acid to N-acetyl-L-phenylalanine provided results as shown in Table II.

TABLE II

| Bis Phosphine Compound of | Optical Purity (%) | |
|---|---|---|
| | With Base | Without Base |
| Example 7 | 59 | 38 |
| Example 8 | 35 | 52 |

While the invention has been described herein with regard to certain specific embodiments, it is not so limited. It is to be understood that variations and modifications thereof may be made by those skilled in the art without departing from the spirit and scope of the invention.

The embodiments of this invention is which a particular property or privilege is claimed are defined as follows:

1. In a process for catalytically asymmetrically hydrogenating a β-substituted-α-acylamido-acrylic acid and/or its salts, esters or amides in the presence of a homogeneous, optically active catalyst having an optically active phosphine ligand in order to afford a desired optical enantiomorph in at least about 89.4% optical purity, the improvement wherein the catalyst is a coordinated complex catalyst comprising a transition metal selected from the group consisting of rhodium, iridium and ruthenium in combination with from about 0.5 to about 2.0 moles per mole of metal of an optically active bis phosphine ligand represented by the structural formula

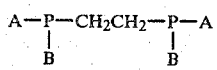

wherein A and B each independently represent substituted and unsubstituted alkyl of from 1 to 12 carbon atoms, substituted and unsubstituted cycloalkyl having from 4 to 7 carbon atoms or substituted and unsubstituted aryl; provided that such substituents provide no significant interference with the steric requirements around the phosphorus atom and A and B are different.

2. In a process according to claim 1, the improvement wherein the transition metal is rhodium.

3. In a process according to claim 1, the improvement wherein A and B are dissimilar aryl groups.

4. In a process according to claim 3, the improvement wherein the transition metal is rhodium.

5. In a process according to claim 3, the improvement wherein one of said dissimilar aryl groups has an alkoxy substituent at the ortho position.

6. In a process according to claim 5, the improvement wherein the transition metal is rhodium.

7. In a process according to claim 1, the improvement wherein the bis phosphine is represented by the structural formula

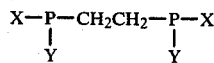

wherein
X represents substituted and unsubstituted phenyl,
Y represents substituted and unsubstituted 2-alkoxyphenyl wherein the alkoxy has from 1 to 6 carbon atoms; provided that such substituents provide no significant interference with the steric requirements around the phosphorus atom and X and Y are different.

8. In a process according to claim 7, the improvement wherein the transition metal is rhodium.

9. In a process according to claim 1, the improvement wherein the bis phosphine ligand is represented by the structural formula wherein

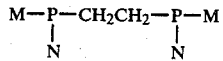

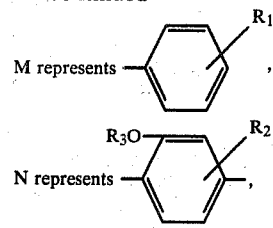

$R_1$ and $R_2$ each independently represent hydrogen, halogen, alkyl having from 1 to 6 carbon atoms and alkoxy having from 1 to 6 carbon atoms, and
$R_3$ represents normal alkyl having from 1 to 6 carbon atoms; provided that M and N are different.

10. In a process according to claim 9, the improvement wherein the transition metal is rhodium.

11. In a process according to claim 1, the improvement wherein the catalyst is a coordinated complex catalyst comprising a transition metal selected from the group consisting of rhodium, iridium and ruthenium in combination with from about 0.5 to about 2.0 moles per mole of metal of optically active 1,2-bis(o-anisylphenylphosphino)ethane.

12. In a process according to claim 11, the improvement wherein the transition metal is rhodium.

13. In a process according to claim 11, the improvement wherein optically active 1,2-bis(o-anisylphenylphosphino)ethane is present in about 1.0 mole per mole of transition metal.

14. In a process according to claim 13, the improvement wherein the transition metal is rhodium.

15. In a process according to claim 1, the improvement wherein the catalyst is a solid, cationic coordination metal complex containing one mole of the optically active bis phosphine ligand per mole of metal, a chelating bis olefin and an anion.

16. In a process according to claim 15, the improvement wherein the transition metal is rhodium.

17. In a process according to claim 3, the improvement wherein the catalyst is a solid, cationic coordination metal complex containing one mole of the optically active bis phosphine ligand per mole of metal, a chelating bis olefin and an anion.

18. In a process according to claim 17, the improvement wherein the transition metal is rhodium.

19. In a process according to claim 5, the improvement wherein the catalyst is a solid, cationic coordination metal complex containing one mole of the optically active bis phosphine ligand per mole of metal, a chelating bis olefin and an anion.

20. In a process according to claim 19, the improvement wherein the transition metal is rhodium.

21. In a process according to claim 7, the improvement wherein the catalyst is a solid, cationic coordination metal complex containing one mole of the optically active bis phosphine ligand per mole of metal, a chelating bis olefin and an anion.

22. In a process according to claim 21, the improvement wherein the transition metal is rhodium.

23. In a process according to claim 9, the improvement wherein the catalyst is a solid, cationic coordination metal complex containing one mole of the optically active bis phosphine ligand per mole of metal, a chelating bis olefin and an anion.

24. In a process according to claim 23, the improvement wherein the transition metal is rhodium.

25. In a process according to claim 11, the improvement wherein the catalyst is a solid, cationic coordination metal complex containing one mole of the optically active bis phosphine ligand per mole of metal, a chelating bis olefin and an anion.

26. In a process according to claim 25, the improvement wherein the transition metal is rhodium.

27. In a process according to claim 13, the improvement wherein the catalyst is a solid, cationic coordination metal complex containing one mole of the optically active bis phosphine per mole of metal, a chelating bis olefin and an anion.

28. In a process according to claim 27, the improvement wherein the transition metal is rhodium.

29. In a process according to claim 1, the improvement wherein the catalyst comprises a solution of a transition metal selected from the group consisting of rhodium, iridium and ruthenium and the optically active bis phosphine ligand.

30. In a process according to claim 29, the improvement wherein the transition metal is rhodium.

31. In a process according to claim 3, the improvement wherein the catalyst comprises a solution of a transition metal selected from the group consisting of rhodium, iridium and ruthenium and the optically active bis phosphine ligand.

32. In a process according to claim 31, the improvement wherein the transition metal is rhodium.

33. In a process according to claim 5, the improvement wherein the catalyst comprises a solution of a transition metal selected from the group consisting of rhodium, iridium and ruthenium and the optically active bis phosphine ligand.

34. In a process according to claim 33, the improvement wherein the transition metal is rhodium.

35. In a process according to claim 7, the improvement wherein the catalyst comprises a solution of a transition metal selected from the group consisting of rhodium, iridium and ruthenium and the optically active bis phosphine ligand.

36. In a process according to claim 35, the improvement wherein the transition metal is rhodium.

37. In a process according to claim 9, the improvement wherein the catalyst comprises a solution of a transition metal selected from the group consisting of rhodium, iridium and ruthenium and the optically active bis phosphine ligand.

38. In a process according to claim 37, the improvement wherein the transition metal is rhodium.

39. In a process according to claim 11, the improvement wherein the catalyst comprises a solution of a transition metal selected from the group consisting of rhodium, iridium and ruthenium and the optically active bis phosphine ligand.

40. In a process according to claim 39, the improvement wherein the transition metal is rhodium.

41. In a process according to claim 13, the improvement wherein the catalyst comprises a solution of a transition metal selected from the group consisting of rhodium, iridium and ruthenium and the optically active bis phosphine ligand.

42. In a process according to claim 41, the improvement wherein the transition metal is rhodium.

43. In a process according to claim 1, the improvement wherein the catalyst is cyclooctadiene-1,5-[1,2-bis-(o-anisylphenylphosphino)ethane] rhodium tetrafluoroborate.

44. In a process according to claim 1, the improvement wherein the catalyst is a catalyst solution containing (a) bis(cyclooctadiene-1,5)-dichlorodirhodium and (b) optically active 1,2-bis(o-anisylphenyl-phosphino)ethane.

45. In a process according to claim 44, the improvement wherein the mole ratio of (a) to (b) is from about 0.25 to about 1.

46. In a process according to claim 45, the improvement wherein the mole ratio of (a) to (b) is about 0.5.

* * * * *

UNITED STATES PATENT AND TRADEMARK OFFICE
CERTIFICATE OF CORRECTION

PATENT NO. : 4,220,590

DATED : September 2, 1980

INVENTOR(S) : William S. Knowles, Milton J. Sabacky and Billy D. Vineyard

It is certified that error appears in the above-identified patent and that said Letters Patent are hereby corrected as shown below:

Column 9, line 36, "anc" should read -- and --.

Columns 9/10, Table I, "Solvent" should be above the second column of the table starting with "Methanol".

Column 12, line 47, the word "cyclohexylphsophino" should read -- cyclohexylphosphino --

Column 13, Claim 7, line 2, after "phosphine" insert "ligand"

Column 13, Claim 9, line 4, the word "wherein" should be located after the structural formula.

Column 15, Claim 27, line 4, after "phosphine" insert "ligand"

Signed and Sealed this

Twenty-fifth Day of November 1980

[SEAL]

Attest:

SIDNEY A. DIAMOND

Attesting Officer

Commissioner of Patents and Trademarks